United States Patent [19]

Franke et al.

[11] Patent Number: 4,921,874
[45] Date of Patent: May 1, 1990

[54] MEDICINAL BATH OILS

[75] Inventors: Rolf Franke, Reinbek; Peter Schmersahl, Willinghusen, both of Fed. Rep. of Germany

[73] Assignee: Merck Patent Gesellschaft mit Beschrankter Haftung, Darmstadt, Fed. Rep. of Germany

[21] Appl. No.: 86,181

[22] Filed: Aug. 17, 1987

Related U.S. Application Data

[63] Continuation of Ser. No. 722,089, Apr. 11, 1985, abandoned.

[30] Foreign Application Priority Data

Apr. 11, 1984 [DE] Fed. Rep. of Germany ....... 3413563

[51] Int. Cl.$^5$ .......................... A61K 7/48; A61K 7/50; A61K 9/10
[52] U.S. Cl. .................................. 514/552; 514/861; 514/865; 514/873; 514/887; 514/939
[58] Field of Search ................................ 514/939, 552

[56] References Cited

U.S. PATENT DOCUMENTS

| | | | |
|---|---|---|---|
| 4,017,615 | 4/1977 | Shastri et al. | 514/172 |
| 4,105,783 | 8/1978 | Yu | 514/459 |
| 4,529,605 | 7/1985 | Lynch et al. | 514/552 |
| 4,626,529 | 12/1986 | Grollier | 514/159 |

FOREIGN PATENT DOCUMENTS 158108 10/1985 European Pat. Off. .

OTHER PUBLICATIONS

Chem. Abst., 86:60420x, (1976).
*Cosmetics & Toiletries*, vol. 94, Jul. 1979, pp. 55, 58 and 78, (1979).
Harry's, *Cosmetic Materials*, pp. 52–53, (1963).
*Merck Index* 9th ed., Abstracts 6858 & 8502, (1976).
*Handbook of Nonprescription Drugs*, 6th ed., pp. 400–1 and 407, (1979).

*Primary Examiner*—Dale R. Ore
*Attorney, Agent, or Firm*—Millen, White & Zelano

[57] ABSTRACT

There is described a medicinal bath oil containing about 68–95 percent by weight of one or more physiologically acceptable oil and about 30–5 percent by weight of one or more physiologically acceptable emulsifiers, at least one of which is a fatty alcohol polygolyol ether.

23 Claims, No Drawings

MEDICINAL BATH OILS

This application is a continuation of application Ser. No. 722,089 filed Apr. 11, 1985, now abandoned.

BACKGROUND OF THE INVENTION

This invention relates to medicinal bath oils.

As is known, medicinal bath oils are used by patients with a dry skin in order to avoid the loss of skin lipids, which occurs on washing with soaps or synthetic detergents. A frequency concomitant phenomenon in skin disorders associated with dry skin is pruritus, which frequently persists even when a medicinal bath oil is used, necessitating use also of a local anaesthetic.

SUMMARY OF THE INVENTION

It is an object of the present invention to provide a medicinal oil bath, which of itself has an antipruritic effect.

Upon further study of the specification and appended claims, further objects and advantages of this invention will become apparent to those skilled in the art.

These objects have been achieved by providing a medicinal bath oil which comprises about 68–95% by weight of one or more physiologically acceptable oils and about 30–5% by weight of one or more physiologically acceptable fatty alcohol polyglycol ether emulsifiers.

DETAILED DISCUSSION

The bath oils according to the invention contain about 68–95, preferably about 80–85, percent by weight of one or more of the oils, and about 30–5, preferably about 20–15, percent by weight of emulsifiers. One or more, preferably two or three, of the emulsifiers can be present. The mixture of the emulsifiers used preferably has a hydrophile-lipophile balance (HLB value) in the range of about 12 to 14.

Suitable physiologically acceptable oils are all vegetable and mineral oils customary in pharmacy. The former are especially preferred, in particular soya oil, also arachis oil; among the mineral oils, liquid paraffin is preferred.

Preferred fatty alcohol polyglycol ethers correspond to the general formula $R—(O—CH_2CH_2)_n—OH$, in which R is an alkyl radical preferably having 16–18, in particular, 10–14, C atoms and n is an integer between 2 and 15, preferably between 4 and 12. Lauryl polyglycol ethers ($R=C_{12}H_{25}$), which are commercially available, for example, under the name Laureth n, such as Laureth 4, Laureth 9 and Laureth 10, are particularly preferred; as a rule, these are mixtures, the figure n indicating the mean number of ethylene oxide groups. Laureth 9 is particularly preferred; a mixture whose composition can be described by the approximate formula $C_{12}H_{15}—(OCH_2CH_2)_9—OH$ is polidocanol, and this is also particularly preferred.

The local anaesthetic and antipruritic effects of some of these fatty aclohol polyglycol ethers as such, for example, those of polidocanol, are known. However, it is surprising that these effects still appear at the use concentration of bath oils containing them, namely a dilution with water in the ratio of about 1:5000. At this use concentration, the active fatty alcohol polyglycol ethers are present in the bath water in concentrations of only about 0.0025 to 0.015%. It could not have been predicted that these ethers would still be effective against pruritus at these low concentrations.

The bath oils according to the invention can contain conventional additives, for example, other emulsifiers; preservatives; antioxidants, such as BHT (butylated hydroxytoluene) or BHA (butylated hydroxyanisole); solubilisers, for example, alcohols, such as isopropanol or 2-octyl-1-dodecanol, polyethylene glycols and their esters, for example, their oleates, fatty acid mono-, di- or polyalkylolamides; stabilizers, such as hectorite.

The local anaesthetic effect of the bath oils according to the invention can be determined by, for example, testing the corneal reflex of the rabbit eye by a method derived from that of Regnier (see M. J. Regnier, C.R. Acad. Sci. Paris 177, 558–560, 1923; Th. Eckert and E. Wachtel, Arzneimittelforschung/Drug Res. 33, 98–100, 1983), and on the human lower lip and tongue using an electrical stimulator (lip and tongue stimulation test).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. The numbers in front of the individual constituents in the formulation examples which follow denote parts by weight.

EXAMPLE 1

5: Laureth 4
5: Laureth 9
5: Laureth 10
83.75: soya oil
1: perfume
0.25: BHT (butylated hydroxytoluene)

EXAMPLE 2

5: Laureth 9
94.75: soya oil
0.25: BHA (butylated hydroxyanisole)

EXAMPLE 3

25: Laureth 4
5: Laureth 9
68.75: soya oil
1: perfume
0.25: BHT

EXAMPLE 4

5: Laureth 4
5: Laureth 9
5: Laureth 10
82.95: soya oil
1: perfume
0.05: BHT
0.9: BHT
0.1: liquid paraffin
0.1: hectorite

EXAMPLE 5

4.5: Laureth 4
4.5: Laureth 9
4.5: Laureth 10
45: soya oil
31.45: arachis oil
1: perfume
0.05: BHT
4.5: isopropanol 4.5: 2-octyl-1-dodecanol

EXAMPLE 6

15: Laureth 9
33.95: arachis oil
50: liquid paraffin
1: perfume
0.05: BHT

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A medicinal bath oil for effecting an antipruritic effect in a bath of water, consisting of about 68–95% by weight of at least one physiologically acceptable oil and about 30–5% by weight of at least three physiologically acceptable fatty alcohol polyglycol ether emulsifiers, the amount of said emulsifiers being sufficient to induce an improved local anesthetic and antipruritic effect.

2. A medicinal bath oil according to claim 1, wherein the physiologically acceptable oils are vegetable oils and mineral oils.

3. A medicinal bath oil according to claim 2, wherein the physiologically acceptable oil is a vegetable oil.

4. A medicinal bath oil according to claim 3, wherein the vegetable oil is soya oil.

5. A medicinal bath oil according to claim 3, wherein the vegetable oil is arachis oil.

6. A medicinal bath oil according to claim 2, wherein the physiologically acceptable oil is liquid paraffin oil.

7. A medicinal bath oil according to claim 1, wherein the fatty alcohol polyglyol ethers are of the formula $R-(O-CH_2CH_2)_n-OH$, wherein R is alkyl having 6–18 carbon atoms and n is an integer between 2 and 15.

8. A medicinal bath oil according to claim 7, wherein the fatty alcohol polyglycol ethers include a mixture of a first ether wherein n is 2–4 and a second ether wherein n is 9–15.

9. A medicinal bath oil according to claim 8, wherein R is $C_{12}H_{25}$ and n is 4 in the first ether and 9 or 10 in the second ether.

10. A medicinal bath oil according to claim 7, wherein R is alkyl having 10–14 carbon atoms and n is an integer between 4 and 12.

11. A medicinal bath oil according to claim 7, wherein R is $C_{12}H_{25}$ and n is 9 or 10.

12. A medicinal bath oil according to claim 1, wherein the fatty alcohol polyglycol ether emulsifier is a lauryl polyglycol ether.

13. A medicinal bath oil according to claim 1, wherein hydrophile-lipophile balance of the emulsifiers is in the range of about 12 to 14.

14. A medicinal bath oil consisting essentially of about 83.75 to 83.95 percent by weight of at least one physiologically acceptable oil and 15 percent by weight of equal amounts of three physiological acceptable fatty alcohol polyglycol ether emulsifers of the formula $C_{12}H_{15}-(O-CH_2CH_2)_n-OH$, wherein n is 4 in the first ether, 9 in the second ether and 10 in the third ether.

15. A medicinal bath oil according to claim 14, consisting of about 83.75 to 83.95 percent by weight of at least one physiologically acceptable oil and 15 percent by weight of equal amounts of three physiological acceptable fatty alcohol polyglycol ether emulsifiers of the formula $C_{12}H_{15}-(O-CH_2CH_2)_n-OH$, wherein n is 4 in the first ether, 9 in the second ether and 10 in the third ether.

16. A medicinal bath containing about 1 part by weight of a medicinal bath oil of claim 14 and 5000 parts by weight of water.

17. A medicinal bath containing about 1 part by weight of a medicinal bath oil of claim 1 and 5000 parts by weight of water.

18. A medicinal bath according to claim 17, containing 0.0025% to 0.015% by weight of fatty alcohol polyglycol ether emulsifiers.

19. A medicinal bath containing water and a concentration of a medicinal bath oil of claim 1, wherein said fatty alcohol polyglycol ethers are present in an amount effective against pruritus.

20. A method of alleviating dry skin in a patient which comprises bathing the patient in the medicinal bath of claim 19.

21. A method of treating pruritus in a patient which comprises bathing the patient in the medicinal bath of claim 16.

22. A method of alleviating dry skin in a patient which comprises bathing the patient in the medicinal bath of claim 17.

23. A method of treating pruritus in a patient which comprises bathing the patient in the medicinal bath of claim 17.

* * * * *